United States Patent [19]

Kessels

[11] 4,215,223
[45] Jul. 29, 1980

[54] PROCESS FOR THE PREPARATION OF D(-)αPHENYLGLYCINE

[76] Inventor: Gerard Kessels, Slekkerstraat 8, Echt (L.), Netherlands

[21] Appl. No.: 951,483

[22] Filed: Oct. 16, 1978

[30] Foreign Application Priority Data

Oct. 18, 1978 [NL] Netherlands ............... 7711396

[51] Int. Cl.² ........................................... C07B 20/00
[52] U.S. Cl. ................................. 562/401; 562/444
[58] Field of Search ........................... 562/401, 444

[56] References Cited

U.S. PATENT DOCUMENTS

| | | | |
|---|---|---|---|
| 2,561,284 | 7/1951 | Long | 562/401 |
| 3,221,046 | 11/1965 | Johnson et al. | 562/401 |
| 3,448,144 | 6/1969 | Okano et al. | 562/401 |
| 3,828,049 | 8/1974 | Karady et al. | 562/401 |
| 4,016,205 | 4/1977 | Kariyone et al. | 562/401 |
| 4,111,980 | 9/1978 | Boesten | 562/401 |

*Primary Examiner*—Norman Morgenstern
*Assistant Examiner*—Vera C. Clarke
*Attorney, Agent, or Firm*—Kane, Dalsimer, Kane, Sullivan and Kurucz

[57] ABSTRACT

The invention provides a process for the preparation of D(-)αphenylglycine by resolution of DLαphenylglycine by means of D(+)camphorsulfonic acid. The present process enables the preparation of D(-)αphenylglycine at a minimum loss of the very expensive starting materials, such as DLαphenylglycine and D(+)camphorsulfonic acid. The salts produced in this process are precipitated from the resolution filtrate and the filtrate may be discarded as effluent water without any danger to the environment.

4 Claims, 1 Drawing Figure

FLOW SHEET
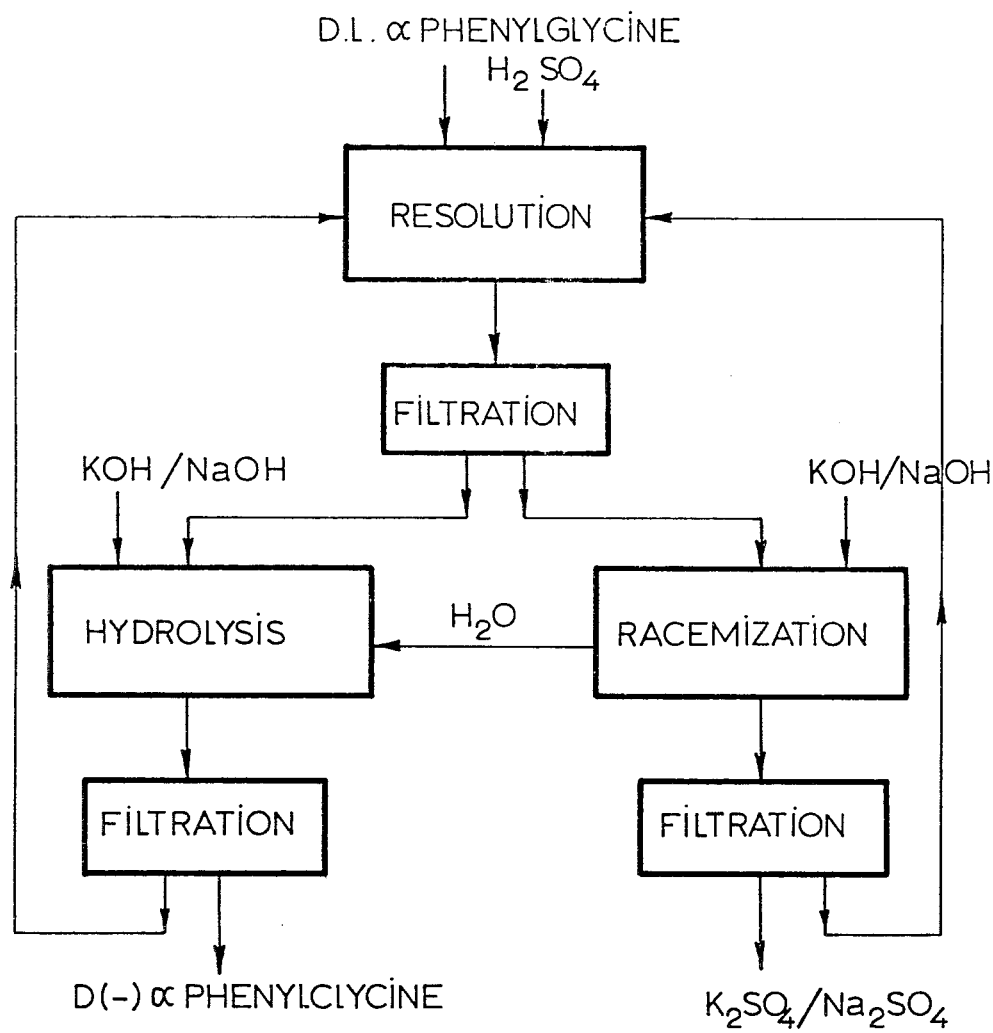

PROCESS FOR THE PREPARATION OF D(-)αPHENYLGLYCINE

BACKGROUND OF THE INVENTION

1. Field of the Invention

The present invention relates to a process of the preparation of D(−)αphenylglycine by resolution of DLαphenylglycine by means of D(+)camphorsulfonic acid in the presence of a strong acid in a reaction vessel, wherein the crystallized salt of the D(−)αphenylglycine is filtrated and then it is subjected to hydrolysis by the addition of a base whereby the D(−)αphenylglycine precipitates and finally said D(−)αphenylglycine is recovered and the obtained filtrate containing the salt of the D(−)camphorsulfonic acid dissolved in water, is introduced again into the reaction vessel, whereas the filtrate, obtained after filtration of the salt of the D(−)αphenylglycine, which filtrate contains L(+)α-phenylglycine, is subjected to an alkaline racemization by means of a base, wherein the obtained DLαphenylglycine is also introduced into the reaction vessel.

2. Brief Description of the Prior Art

The preparation of D(−)αphenylglycine by resolution of a racemic mixture of DLαphenylglycine into the D and L isomers by means of D(+)camphorsulfonic acid is known.

Also the alkaline racemization of the undesired L isomer in the racemic DL mixture is known.

The known process for the preparation of D(−)α-phenylglycine, wherein subsequent to the racemization the mixture is neutralized and filtrated, whereas the solid DLαphenylglycine is introduced again into the reaction vessel and the filtrate is removed as effluent water, has as disadvantages that together with the filtrate salts, very expensive DLαphenylglycine and especially D(+)camphorsulfonic acid are discarded, which means, that the known process on the one hand is uneconomical because of the loss of expensive starting materials, which from time to time have to be supplemented and otherwise said process causes pollution of the environment.

An object of the present invention is to eliminate the above mentioned disadvantages efficiently.

SUMMARY OF THE INVENTION

In accordance with the invention $H_2SO_4$ is used as strong acid, whereas the L(+)αphenylglycine without separation from the racemization mixture is subjected to racemization in the presence of the D(+)camphorsulfonic acid by means of KOH or NaOH, wherein during the racemization, which is carried out at increased temperatures, water is removed by distillation which water is used for the hydrolysis whereupon the racemization mixture is chilled under crystallization of $K_2SO_4$ or $Na_2SO_4$, which is recovered by crystallization and the obtained filtrate, containing the K- or Na-salt of the DLαphenylglycine and the K- or Na-salt of the camphorsulfonic acid, dissolved in water, is introduced again into the reaction vessel, whereupon the DLαphenylglycine is supplemented and additional sulphuric acid is added, obtaining a mixture to be resoluted again.

BRIEF DESCRIPTION OF THE DRAWING

The accompanying drawing is a flow sheet showing schematically the process of the invention.

DETAILED DESCRIPTION OF THE INVENTION

In accordance with the present process essentially any loss of D(−)αphenylglycine and D(+)camphorsulfonic acid is prevented, whereas furthermore no process effluent water is discarded, which means that no pollution of the environment occurs.

The according to the present process obtained solid salts, such as $K_2SO_4$ in use of KOH or $Na_2SO_4$ in use of NaOH, are separated from the racemic mixture by filtration and may be used for other purposes, for instance as fertilizer in the agriculture in case of $K_2SO_4$.

The process of the invention is illustrated by means of the enclosed working scheme.

To the starting resolution mixture in the reaction vessel $H_2SO_4$ is added besides the DLαphenylglycine in order to convert the recovered K- or Na-salt of D(+)camphorsulfonic acid into the free acid, to neutralize the alkaline racemization mixture and to dissolve the newly added DLαphenylglycine.

To the crystallized salt of D(−)αphenylglycine and D(+)-camphorsulfonic acid KOH or NaOH and water are added after separation from the resolution mixture, wherein the D(−)αphenylglycine is precipitated and the K- or Na-salt of D(+)camphorsulfonic acid is dissolved.

After precipitation of the desired D(−)αphenylglycine, the solution of the K- or Na-salt of D(+)camphorsulfonic acid is introduced again into the reaction vessel and therein it is used again for a subsequent resolution.

The filtrate of the resolution mixture contains the excess of D(+)camphorsulfonic acid, D(+)αphenylglycine and $KHSO_4$ or $NaHSO_4$. By addition of KOH or NaOH the pH of the mixture is adjusted to a value of 11 or higher, preferably on a value of 11–13.

The mixture is cooked during 1.5–4 hours at a temperature of 100°–120° C. in order to racemize the L isomer into DL. Simultaneously a part of the water from the racemization mixture is removed by distillation in order to prevent the volume increase of the process liquid. The distilled water is used for the washing of the several filtrated solid materials and for the hydrolysis of the salt of D(−)αphenylglycine and D(+)camphorsulfonic acid.

By chilling the racemization mixture to 18°–30° C. the $K_2SO_4$ or $Na_2SO_4$ present in the process liquid surprisingly crystallizes essentially quantitatively and may be separated by means of a simple filtration. The $Na_2SO_4$ crystals contain 10 mol of crystallization water. The liquid containing DLαphenylglycine and the K- or Na-salt of D(+)camphorsulfonic acid is introduced again into the reaction vessel and it is used again in the subsequent resolution.

The process of the invention is illustrated in more detail by means of the following examples.

EXAMPLE I

1st resolution (KOH)

In a reaction vessel the following mixture is stirred:
1200 ml of water
2 mole (302 g) of DLαphenylglycine
1.2 mol (278.5 g) of D(+)camphorsulfonic acid
0.8 mole (78.4 g) of $H_2SO_4$.

The resolution mixture was heated under stirring to 90°–100° C., wherein the DLαphenylglycine is dissolved.

Then the solution is cooled to 15°–30° C. under stirring, wherein the salt of D(−)αphenylglycine has been crystallized.

The crystals were filtrated and washed with a slight amount of water. Yield of the salt was about 300 g.

Hydrolysis

The salt formed during the resolution was stirred in 500 ml of water. By addition of circa 42 g of KOH dissolved in 60 ml of water, the pH of the mixture is adjusted on a value of 3.5–6. The reaction mixture was cooled and the crystallized D(−)αphenylglycine was filtrated.

The crystals were washed on the filter by means of a slight amount of water.

The product was dried. Yield: 118 g; content via acid-base titration amounts 99%. Specific rotation $[\alpha] D/20 = -160°$.

Racemization

The filtrate of the resolution mixture plus the wash liquid were stirred and made alkaline to a pH more than 11 by means of circa 3.22 mol (185 g) of KOH.

For the racemization the mixture is then heated to 100°–120° C. during 3 hours, wherein sufficient water is distilled off in order to decrease the volume to ±900 ml. Then the mixture was cooled to 20° C. under stirring. Herein $K_2SO_4$ crystallized and by filtration separated. The crystals were washed by means of a slight amount of water, which has been distilled off during the racemization.

Yield of $K_2SO_4$ circa 136 g.

The filtrate circa 750 ml was introduced again into the reaction vessel and used again during the following resolution.

EXAMPLE II

2nd and following resolution

In the reaction vessel of Example I the following mixture is stirred:

the filtrate obtained after the hydrolysis in Example I, which filtrate contained 0.8 mol (217 g) of K-salt of D(+)camphorsulfonic acid in water and a slight amount of D(−)αphenylglycine. Volume circa 1400 ml.

the filtrate, obtained after the filtration of the racemization mixture in Example I, which filtrate contained 1.2 mol (181.4 g) of DLαphenylglycine, 0.4 mol (108.5 g) of K-salt of D(+)camphorsulfonic acid, 1.22 mol (68.4 g) of KOH dissolved in water. Total volume circa 750 ml.

8.8 mol (120.9 g) of DLαphenylglycine, (a new portion).

4.4 mol (431.2 g) of $H_2SO_4$. (a new portion).

The resolution mixture was heated under stirring to 90°–100° C., whereas the DLαphenylglycine is dissolved.

Then the solution was cooled to 15°–30° C. under stirring, whereas the salt of D(−)αphenylglycine crystallized out. The crystals were filtrated and washed by means of a slight amount of water, which has been distilled off during the former racemization. Yield of salt circa 307 g.

Hydrolysis

The salt formed during the resolution was stirred in 500 ml of water which has been distilled off during the previous racemization. By addition of circa 45 g of KOH dissolved in 60 ml of water the pH of the mixture has been adjusted on 3.5–6. The reaction mixture was cooled to 15°–35° C., whereas the crystallized D(−)αphenylglycine was filtrated.

The crystals were washed on the filter with a slight amount of water, which has been distilled off during the previous racemization. The product was dried. Yield: 121 g; content via acid-base titration 99%. Specific rotation $[\alpha] D/20 = -160°$.

Racemization

The filtrate of the resolution mixture plus the wash liquid were stirred and made alkaline to a pH of more than 11 by means of 8 mol (449 g) of KOH.

Prior to the racemization the mixture was heated to 100°–120° C. during 3 hours, wherein sufficient water was distilled off in order to obtain a volume of circa 950 ml. Then the mixture was cooled off to 20° C. under stirring. Herein $K_2SO_4$ crystallized out, which was separated by filtration. The crystals were washed with a slight amount of water, which has been distilled off during the racemization.

Yield of $K_2SO_4$ after drying circa 766 g.

The filtrate circa 750 ml was introducted again into the reaction vessel and used again in the following resolution.

EXAMPLE III

1st Resolution

In a reaction vessel the following mixture is stirred:
1200 ml of water
2 mol (302 g) of DLαphenylglycine
1.2 mol (278.5 g) of D(+)camphorsulfonic acid
0.8 mol (78.4 g) of $H_2SO_4$.

The resolution mixture was heated under stirring to 90°–100° C., wherein the DLαphenylglycine is dissolved.

Then the solution was cooled off to 15°–30° C. under stirring, wherein the salt of D(−)αphenylglycine crystallized out.

The crystals were filtered and washed with a slight amount of water. Yield of salt circa 300 g.

Hydrolysis

The salt formed during the resolution was stirred in 500 ml of water. By addition of circa 31 g of NaOH dissolved in 55 ml of water the pH of the mixture was adjusted on 3.5–6. The reaction mixture was cooled off and the crystallized D(−)αphenylglycine was filtrated.

The crystals were washed on the filter with a slight amount of water. The product was dried. Yield: 118 g; content via acid-base titration 99%. Specific rotation $[\alpha] D/20 = -160°$.

Racemization

The filtrate of the resolution mixture plus the wash liquid were stirred and made alkaline to a pH of more than 11 by means of 3.22 mol of NaOH (129 g).

For the racemization the mixture is heated to 100°–120° C. during 3 hours, wherein sufficient water has been distilled off in order to decrease the volume to circa 850 ml. Then the mixture was cooled off to 20° C. under stirring. Herein $Na_2SO_4.10H_2O$ crystallized out, which material was separated by filtration. The crystals were washed with a slight amount of water, which has been distilled off during the racemization. Yield: $Na_2SO_4.10H_2O$ circa 259 g.

The filtrate circa 750 ml was introduced into the reaction vessel and used again during the following resolution.

EXAMPLE IV

2nd and following resolution

In a reaction vessel the following mixture was stirred:

the filtrate obtained during the hydrolysis in Example III, which filtrate contained 0.8 mol (203.2 g) of Na-salt of D(+)camphorsulfonic acid in water and a slight amount of D(−)α-phenylglycine. Volume circa 700 ml.

the filtrate, obtained after the filtration of the racemization mixture in the previous preparation, which filtrate contained 1.2 mol (181.4 g) of DL(α)-phenylglycine, 0.4 mol (101.6 g) of Na-salt of D(+)camphorsulfonic acid, 1.22 mol (48.8 g) of NaOH dissolved in water. Total volume circa 750 ml.

0.8 mol (120.9 g) of DLα-phenylglycine (a new portion)

4.4 mol (431.2 g) $H_2SO_4$ (a new portion)

The resolution mixture was heated to 90°–100° C., under stirring, wherein the DLα-phenylglycine is dissolved.

Subsequently the solution was cooled off to 15°–30° C. under stirring, wherein the salt of D(−)α-phenylglycine and D(+)-camphorsulfonic acid crystallized out. The crystals were filtrated and washed with a slight amount of water. Yield of salt circa 307 g.

Hydrolysis

The salt formed during the resolution was stirred in 500 ml of water, which has been distilled off during the previous racemization. By addition of circa 32 g of NaOH dissolved in 54 ml water the pH of the mixture has been adjusted to 3.5–6.

The reaction mixture was cooled off to 15°–35° C. and the crystallized D(−)α-phenylglycine was filtrated.

The crystals were washed on the filter with a slight amount of water. The product was dried. Yield: 121 g; content via acid-base titration 99%. Specific rotation $[\alpha]D/20 = -160°$.

Racemization

The filtrate of the resolution mixture plus the wash liquid were stirred and made alkaline to a pH of more than 11 by means of circa 8 mol (320 g) of NaOH.

For the racemization the mixture is heated to 100°–120° C. during 3 hours, wherein sufficient water was distilled off in order to decrease the volume to 1500 ml. Then the mixture was cooled off to 18° C. under stirring. Herein $Na_2SO_4.10H_2O$ crystallized out, which salt has been separated by filtration. The crystals were washed with a slight amount of water. Yield of $Na_2SO_4.10H_2O$ circa 1416 g.

The filtrate circa 750 ml was introduced again into the reaction vessel and used again during the following resolution.

I claim:

1. A process for the resolution and preparation of D(−)α-phenylglycine, which comprises:
   (a) providing a first resolution mixture of D,L-α-phenylglycine in aqueous solution with D(+) camphorsulfonic acid;
   (b) resolving the D,L-α-phenylglycine in the provided mixture, in the presence of a strong acid;
   (c) precipitating the acid salt of the strong acid and D(−)-α-phenylglycine in the resolution mixture obtained in step (b);
   (d) separating the precipitated salt from the resolution mixture, leaving an aqueous residue which comprises L(+)α-phenylglycine in solution with D(+) camphorsulfonic acid;
   (e) dissolving the separated salt in water, obtained as specified in step (i) below;
   (f) hydrolysing the dissolved salt, to obtain D(−)α-phenylglycine;
   (g) separating the D(−)-α-phenylglycine obtained in step (f) from the product hydrolysis reaction mixture obtained in step (f), leaving a residue which comprises the salt of D(−) camphorsulfonic acid in aqueous solution;
   (h) racemizing the L(+)α-phenylglycine in the residue solution left from step (d), to obtain the salt of D,L-α-phenylglycine in solution, in the presence of a base selected from the group consisting of sodium and potassium hydroxide;
   (i) stripping water from the aqueous residue of step (d) while carrying out the racemization of step (h) and using the stripped water to dissolve the salt in step (e) above;
   (j) separating potassium or sodium sulfite from the racemization reaction mixture obtained after steps (h) and (i), leaving an aqueous residue mixture which comprises in solution the salt of D,L-α-phenylglycine and the salt of D(+) camphorsulfonic acid;
   (k) combining the residue solution obtained in step (j) with the residue solution obtained in step (g), to form a second resolution mixture;
   (l) supplementing the second resolution mixture, as needed, with additional D,L-α-phenylglycine, to provide another first resolution mixture to be used in step (m) below;
   (m) repeating steps (b)–(m), inclusive, a plurality of times to obtain the desired D(−)α-phenylglycine in the step (g).

2. The process of claim 1 wherein the racemization mixture used in step (h) has a pH within the range of 11–13.

3. The process of claim 2 wherein the racemization is carried out at a temperature of from 100° to 120° C.

4. The process of claim 3 wherein step (j) comprises cooling the reaction mixture to a temperature of from 18° to 30° C.

* * * * *